(12) United States Patent
Boulanger

(10) Patent No.: US 12,378,213 B1
(45) Date of Patent: Aug. 5, 2025

(54) PROCESS FOR THE HYDROGENATION OF CATNIP OIL

(71) Applicant: William Allen Boulanger, Mahomet, IL (US)

(72) Inventor: William Allen Boulanger, Mahomet, IL (US)

(*) Notice: Subject to any disclaimer, the term of this patent is extended or adjusted under 35 U.S.C. 154(b) by 0 days.

(21) Appl. No.: 18/802,055

(22) Filed: Aug. 13, 2024

(51) Int. Cl.
*C07D 311/94* (2006.01)
*B01J 25/02* (2006.01)

(52) U.S. Cl.
CPC .............. *C07D 311/94* (2013.01); *B01J 25/02* (2013.01)

(58) Field of Classification Search
CPC .................................................. C07D 311/94
USPC ....................................................... 549/283
See application file for complete search history.

(56) References Cited

U.S. PATENT DOCUMENTS

| | | |
|---|---|---|
| 7,067,677 B2 | 6/2006 | Manzer |
| 7,375,239 B2 | 5/2008 | Chauhan et al. |
| 7,547,793 B2 | 6/2009 | Hallahan et al. |
| 8,329,229 B2 | 12/2012 | Gonzalez et al. |
| 8,558,015 B2 | 10/2013 | Fisher et al. |
| 8,748,477 B2 | 6/2014 | Scialdone |
| 8,765,975 B2 | 7/2014 | Hutchenson et al. |
| 8,802,870 B2 | 8/2014 | Gonzalez et al. |
| 9,085,747 B2 | 7/2015 | Scialdone et al. |
| 9,521,844 B2 | 12/2016 | Fisher et al. |
| 10,442,785 B2 | 10/2019 | Jackson et al. |
| 2003/0235601 A1 | 12/2003 | Hallahan |
| 2005/0112166 A1 | 5/2005 | Hallahan |
| 2006/0148842 A1 | 7/2006 | Scialdone et al. |
| 2010/0145077 A1 | 6/2010 | Jackson et al. |

OTHER PUBLICATIONS

Kamlesh R. Chauhan, Walter Schmidt *Tetrahedron Letters* 55 (2014) 2534-2536.

*Primary Examiner* — Taofiq A Solola
(74) *Attorney, Agent, or Firm* — King & Partners, PLC

(57) ABSTRACT

A method including the steps of: (a) providing trans-cis nepetalactone; (b) providing sodium bicarbonate; (c) providing water; (d) providing methanol; (e) mixing the trans-cis nepetalactone, the sodium bicarbonate, the water, the methanol as a reaction mixture for approximately 15 hours at ambient temperature and pressure; (f) converting at least 95.2% of the nepetalactone to a ring open ester and/or aldehyde; (g) removing unreacted sodium bicarbonate via filtration; (h) transferring the filtered reaction mixture to a hydrogenation apparatus; (i) charging the hydrogenation apparatus with Raney nickel and/or Urushibara nickel; and (j) hydrogenating the ring open ester and/or aldehyde to generate at least one of DHN1, DHN2, and DHN3.

2 Claims, 2 Drawing Sheets

PROCESS FOR THE HYDROGENATION OF CATNIP OIL

COPYRIGHT NOTICE

This application includes material that is subject to copyright protection. The copyright owner has no objection to the facsimile reproduction by anyone of the patent disclosure, as it appears in the United States Patent and Trademark Office files or records, but otherwise reserves all copyright rights whatsoever.

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A SEQUENCE LISTING

Not applicable.

BACKGROUND OF THE INVENTION

1. Field of the Invention

The present invention relates in general to an improved hydrogenation process, and, more particularly, to an improved process for the hydrogenation of nepetalactones, including, but not limited to, catmint/catnip oil. The process of the present invention is much cleaner and faster than the prior art processes. Moreover, the process of the present invention prevents or substantially prevents the reaction catalyst from being surface modified, deactivated, fouled and/or otherwise compromised so that it can be used multiple times, thus resulting in a significant cost savings.

2. Background Art

Catnip oil is primarily composed of nepetalactones, with the principle minor component being caryophyllene. The chemical structures of these compounds are provided below:

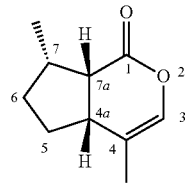

cis-cis nepetalactone (4aR,7S,7aS)-4,7-dimethyl-5,6,7,7a-tetrahydrocyclopenta[c]pyran-1(4aH)-one

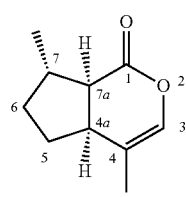

cis-trans nepetalactone (4aS,7S,7aR)-4,7-dimethyl-5,6,7,7a-tetrahydrocyclopenta[c]pyran-1(4aH)-one

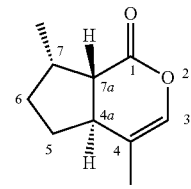

trans-cis nepetalactone (4aS,7S,7aS)-4,7-dimethyl-5,6,7,7a-tetrahydrocyclopenta[c]pyran-1(4aH)-one

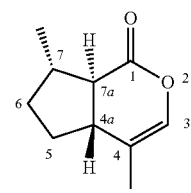

trans-trans nepetalactone (4aR,7S,7aR)-4,7-dimethyl-5,6,7,7a-tetrahydrocyclopenta[c]pyran-1(4aH)-one

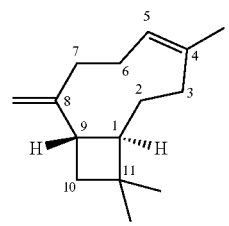

caryophyllene trans-(1R,9S)-8-Methylene-4,11,11-trimethylbicyclo[7.2.0]undec-4-ene When hydrogenated, catnip oil becomes an effective insect repellent. The processes developed at DuPont required palladium catalyst, and higher temperatures and pressures, and this gave a constellation of products, reflecting the many different possible versions of nepetalactones. See, for example, U.S. Pat. No. 10,442,785 entitled Hydrogenation of Catmint Oil, U.S. Pat. No. 9,085,747 entitled Method for the Enhanced Recovery of Catmint Oil, U.S. Pat. No. 8,558,015 entitled Solvent Addition and Removal in the Hydrogenation of Catmint Oil, and U.S. Pat. No. 7,547,793 entitled Method for Making Insect Repellent Composition— which are hereby incorporated herein by reference in their entirety, including all references cited therein. The inventor(s) of the present invention have realized that a polar alcoholic solvent like methanol and catalytic hydroxide assists the hydrogenation by creating an equilibrium between the nepetalactone and the ring-opened ester/aldehyde. The aldehyde is relatively easy to reduce, and once converted to the alcohol, readily ring-closes to the desired dihydronepetalactone under the reaction conditions shown in FIG. 1.

This reaction works well on the bench-top and lesser on the kiloscale due to the high efficiency of the hydrogen transfer. However, with increasing scale, the hydrogen transfer is far less efficient, and alternate paths of reaction appear. One of these events is due to the nature of the nepetalactone itself. Notably, it is notoriously prone to polymerization in the presence of air, via a radical process. The same radical process can also play out in a hydrogenation if the efficiency of the hydrogen saturation in the liquid phase is insufficient, as what happens during scale-up of the reaction. Although this can be partly offset by increasing pressure, the cost of constructing equipment for higher pressure increases according to the square of volume. The consequence is that the nepetalactone polymerizes on the surface of the catalyst, irreversibly deactivating it with time. As the scale increases, more, and more of the Raney nickel must be added to the hydrogenation to achieve completion. This eventually makes the process uneconomical.

On the large scale, even if one keeps adding Raney nickel to finally achieve completion, the reaction takes an alternate path to achieve the final products. This impacts the composition of the final product mixture. It is most desirable to start with the "cis-trans" nepetalactone, which is available either by using the correct cultivar, or via isomerization of the mixture is cis-fused and trans-fused nepetalactones. On the small scale, because the hydrogenation and ring-closure are rapid, the product mixture is almost exclusively the two possible isomers derived of the cis-fused ring system. However, once ring-opened to the methyl ester/aldehyde, this cis arrangement is no longer the most stable, and in the presence of the hydroxide, the methyl ester/aldehyde is isomerized to the more stable trans-form. This trans-form is also kinetically favored in the hydrogenation when nickel is the catalyst. Once hydrogenated, this now ring-closes, but now to the trans-fused dihydronepetalactone, DHN1 (See FIG. 1). In some uses, this is actually a desired outcome, as it modulates species specificity of the product. However, in standard use, it is desirable to have a product mixture mainly of the cis-fused ring products, DHN2 and DHN3 (See FIG. 1). Once DHN1 is formed, it is now less stable than its cis ring system, and continued reaction in the presence of base will slowly (over a period of days at 60° C.) shift the equilibrium to the desired all-cis products.

Unfortunately, this is not the only reaction at play. The hydroxide can also attack and directly hydrolyze the cis- or trans open ester, and make a carboxylate. These can no longer isomerize, so eventually the isomerization stops. The secondary effect is that the hydrolysis also consumes the hydroxide, so eventually, there is no longer any base present for the required isomerization. When this happens, the only known way to solve the problem is to remove the solution from the catalyst, quench with acid, strip off the now-wet methanol, and re-start the hydrogenation with all fresh hydroxide, methanol, and catalyst. This is very expensive, time consuming, and wasteful of materials.

There is also a further complication. Catnip oil that has been derived from cultivars that favor the all trans, cis isomer also comes with a large percentage of nepetalic acid. The chemical structure of nepetalic acid is provided below:

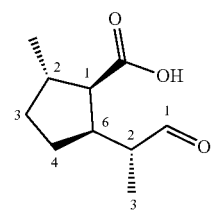

nepetalic acid (1R,2S,5R)-2-methyl-5-[(2R)-1-oxo-propan-2-yl]cyclopentane-1-carboxylic acid The nepetalic acid must be accounted for in the first charging of base in the hydrogenation, or the reaction will commence with insufficient base.

The problem is then how to hydrogenate nepetalactone without exposing the catalyst to nepetalactone, how to accelerate the hydrogenation, while also avoiding unwanted isomerization and hydrolysis. In accordance with the present invention, the answer is to at least substantially, and preferably, totally convert the nepetalactone to the intermediate methyl ester/aldehyde under mild conditions prior to introducing the hydrogenation/reduction catalyst (e.g., Raney nickel). Chauhan and Schmidt have reported that nepetalactone can be totally converted to the ring-opened aldehyde/ester using aqueous methanol and sodium bicarbonate (See Kamlesh R. Chauhan, Walter Schmidt *Tetrahedron Letters* 55 (2014) 2534-2536). While this transformation might be applied to any or a mixture of nepetalactones, use of the trans/cis nepetalactone gives the corresponding cis aldehyde/ester in mild conditions that do not favor isomerization. If an excess of bicarbonate is used, all nepetalic acid present is also converted to the corresponding soluble carboxylate. If Raney nickel is now introduced, it will see no nepetalactone, so this is not present to polymerize on its surface. In accordance with the present invention, and with now the entire reaction mixture starting as the aldehyde, and the catalyst surface now unfettered by polymer, the hydrogenation now runs almost ten times faster. The final benefit is that the nickel catalyst (i.e., Raney nickel, Urushibara nickel, etcetera) may be recovered for re-use without much loss of activity.

After separation of the catalyst, the reaction mixture must be acidified with phosphoric acid to about pH 7 to ring-close the product mixture to DHN2 and DHN3, then filtered to remove the sodium phosphate prior to concentration.

These and other objects of the present invention will become apparent in light of the present specification, claims, and drawings.

SUMMARY OF THE INVENTION

The following presents a simplified summary in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

A method, comprising, consisting essentially of and/or consisting of the steps of: (a) providing a nepetalactone; (b) providing a base; (c) providing a primary solvent; (d) providing a secondary solvent; (e) mixing the nepetalactone, the base, the primary solvent, and the secondary solvent as a reaction mixture for a period of time; (f) converting at least 90% of the nepetalactone to a ring open ester and/or aldehyde; (g) optionally removing unreacted base via filtration; (h) transferring the filtered reaction mixture to a hydrogenation apparatus; (i) charging the hydrogenation apparatus with a reduction catalyst; and (j) hydrogenating the ring open ester and/or aldehyde to generate at least one of DHN1, DHN2, and DHN3.

In a preferred embodiment of the present invention, the step of providing a nepetalactone includes the step of providing trans-cis nepetalactone.

In another preferred embodiment of the present invention, the step of providing a base includes the step of providing sodium bicarbonate and/or an alkali metal hydroxide.

In yet another preferred embodiment of the present invention, the step of providing a primary solvent includes the step of providing distilled water.

In one preferred embodiment of the present invention, the step of providing a secondary solvent includes the step of providing a polar protic alcohol, such as methanol.

In a preferred implementation of the present invention, the step of mixing the reaction mixture for a period of time includes the step of mixing the reaction mixture for at least approximately 12 hours at ambient temperature and pressure.

In another preferred implementation of the present invention, the step of converting at least 90% of the nepetalactone to a ring open ester and/or aldehyde includes the step of converting at least 95.2% of the nepetalactone to a ring open ester and/or aldehyde.

In yet another preferred implementation of the present invention, the step of charging the hydrogenation apparatus with a reduction catalyst includes the step of charging the hydrogenation apparatus with Raney nickel and/or Urushibara nickel.

The present invention is also directed to a hydrogenated product prepared according to the methods disclosed herein.

BRIEF DESCRIPTION OF THE DRAWINGS

Certain embodiments of the present invention are illustrated by the accompanying figures. It will be understood that the figures are not necessarily to scale and that details not necessary for an understanding of the invention or that render other details difficult to perceive may be omitted.

It will be further understood that the invention is not necessarily limited to the particular embodiments illustrated herein.

Figure 1:
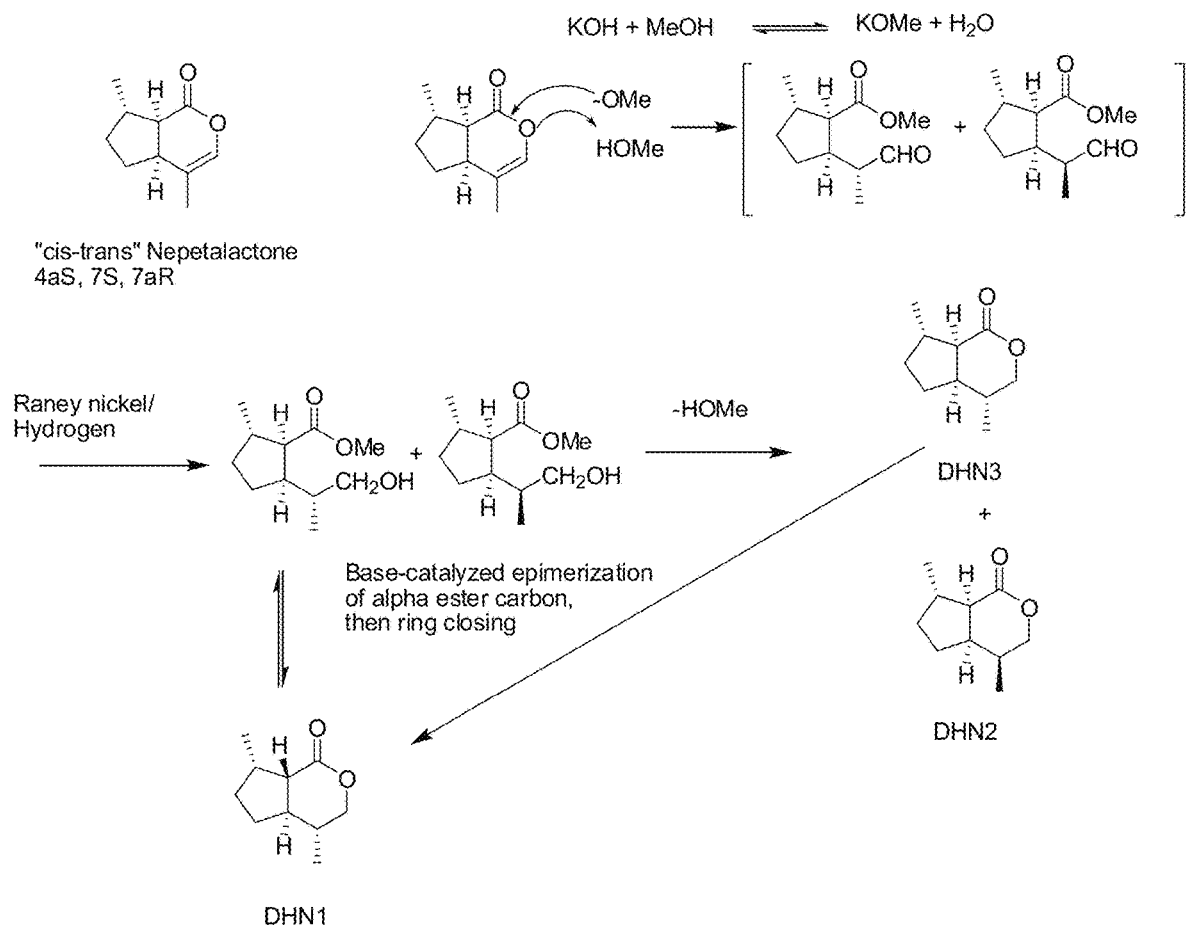
Figure 2:
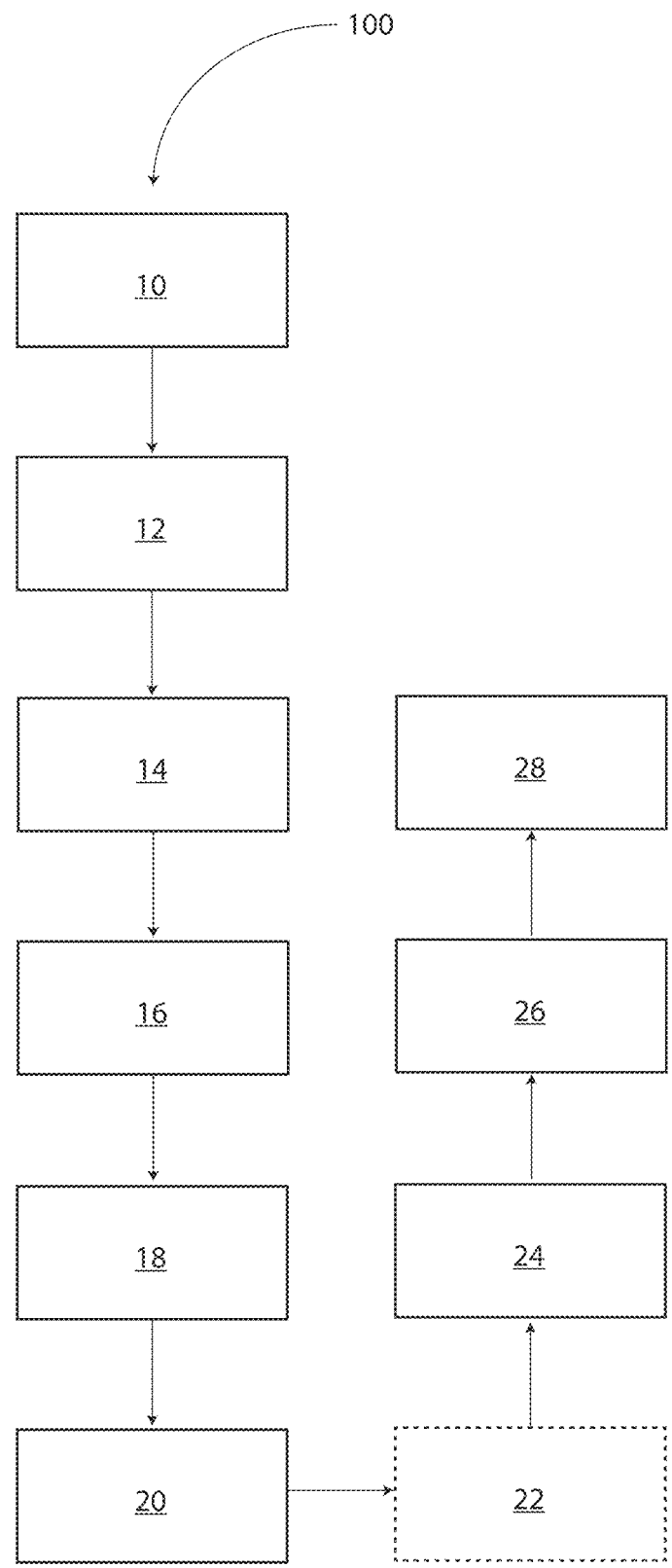

The invention will now be described with reference to the drawings wherein:

FIG. 1 of the drawings is a schematic flowchart for the hydrogenation of catnip oil in accordance with the present invention; and FIG. 2 of the drawings is a flow chart of a method in accordance with the present invention.

DETAILED DESCRIPTION OF THE INVENTION

While this invention is susceptible of embodiment in many different forms, there is shown in the structural formulas and described herein in detail several specific embodiments with the understanding that the present disclosure is to be considered as an exemplification of the principles of the invention and is not intended to limit the invention to the embodiments illustrated. It will be understood that the structural formulas disclosed herein are intended to comprise all stereochemical configurations regardless of graphical representations.

Referring now to FIG. 2, the present invention is directed to method (100) for the hydrogenation/reduction of catnip oil, catmint oil, and/or one or more nepetalactones (e.g., trans-cis nepetalactone), comprising the steps of: (10) providing catnip oil, catmint oil, and/or one or more nepetalactones; (12) providing a base, such as but not limited to a strong base, a weak base, an alkali metal hydroxide, sodium bicarbonate, etcetera; (14) providing a primary solvent, such as a polar solvent, water, distilled water, etcetera; (16) providing a secondary solvent, such as a polar protic solvent, a polar protic alcohol, methanol, ethanol, propanol, butanol, pentanol, hexanol, etcetera; (18) mixing the nepetalactone, the base, the primary solvent, and the secondary solvent as a reaction mixture for a period of time (e.g. approximately (+/−10%) 1, 2, 3, 4, 5, 6, 7, 8, 9, 10, 11, 12, 13, 14, 15, 16, 17, 18, 19, 20, 21, 22, 23, 24, 48, and/or 72 hours, etcetera); (20) converting at least 90% (e.g., 91%, 92%, 93%, 94%, 95%, 95.2%, 96%, 97%, 98%, 99%, 100%, etcetera) of the nepetalactone to a ring open ester and/or aldehyde; (22) optionally removing unreacted base via filtration; (24) transferring and/or introducing the optionally filtered reaction mixture into a hydrogenation apparatus, such as a Parr Shaker, an autoclave, etcetera; (26) charging the hydrogenation apparatus with a reduction catalyst, such as Raney nickel and/or Urushibara nickel; and (28) hydrogenating and/or reducing the ring open ester and/or aldehyde to generate at least one of DHN1, DHN2, and DHN3.

The invention is further described by additional examples and experiments hereinbelow.

Example 1

50 g of trans, cis-nepetalactone (crude), 5 g sodium bicarbonate, 7.5 ml distilled water were combined in 150 mL methanol. The mixture was stirred stoppered at 20° C. overnight (15 hrs). GC analysis showed only 4.8% nepetalactone remaining. The mixture was filtered to remove the unreacted sodium bicarbonate, then charged to a Parr Shaker with 5 g of methanol-washed Raney nickel. It was hydrogenated at 50 psi and 60° C. The hydrogenation was complete in about 1.5 hrs. (Under the hydroxide/methanol conditions, the reaction requires 24-26 hrs). The reaction was stopped, cooled, then filtered to give 55.82 g after filtration. The product was a water-white oil. The slight increase in weight suggests some of the product is in the sodium salt form.

Example 2

50 g of trans, cis-nepetalactone (crude), 5 g sodium bicarbonate, 7.5 ml distilled water were combined in 150 mL methanol. The mixture was stirred stoppered at 20° C. for 18 hrs. GC analysis showed only 2.0% nepetalactone remaining. The mixture was filtered to remove the unreacted sodium bicarbonate, then charged to a Parr Shaker with 5 g of methanol-washed Raney nickel. It was hydrogenated at 50 psi and 60° C. The hydrogenation was complete in about 1.75 hrs. The reaction was stopped, cooled, then filtered to give 56.73 g after filtration. The product was a water-white oil. The slight increase in weight suggests some of the product is in the sodium salt form.

The foregoing description merely explains and illustrates the invention and the invention is not limited thereto except insofar as the appended claims are so limited, as those skilled in the art who have the disclosure before them will be able to make modifications without departing from the scope of the invention.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etcetera shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etcetera. As a non-limiting example, each range discussed herein can be readily broken down into a lower third, middle third and upper third, etcetera. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed and desired to be secured by Letters Patent of the United States is:

1. A method, comprising the steps of:
providing trans-cis nepetalactone;
providing sodium bicarbonate;
providing water;
providing methanol;
mixing the trans-cis nepetalactone, the sodium bicarbonate, the water, the methanol as a reaction mixture for approximately 15 hours at ambient temperature and pressure;
converting at least 95.2% of the nepetalactone to a ring open ester and/or aldehyde;
removing unreacted sodium bicarbonate via filtration;
transferring the filtered reaction mixture to a hydrogenation apparatus;
charging the hydrogenation apparatus with Raney nickel and/or Urushibara nickel; and
hydrogenating the ring open ester and/or aldehyde to generate at least one of DHN1, DHN2, and DHN3.

2. A method, consisting of the steps of:
first, providing trans-cis nepetalactone, sodium bicarbonate, water, and methanol to generate a reaction mixture;
second, mixing the reaction mixture for approximately 15 hours at ambient temperature and pressure;
third, converting at least 95.2% of the nepetalactone within the reaction mixture into a ring open ester and/or aldehyde;
fourth, removing unreacted sodium bicarbonate via filtration;
fifth, charging the filtered reaction mixture to a hydrogenation apparatus;
sixth, charging the hydrogenation apparatus with Raney nickel and/or Urushibara nickel; and
seventh, hydrogenating the ring open ester and/or aldehyde to generate at least one of DHN1, DHN2, and DHN3.

* * * * *